United States Patent [19]

Kiso et al.

[11] Patent Number: 5,034,557
[45] Date of Patent: Jul. 23, 1991

[54] PROCESS FOR PRODUCTION OF AROMATIC CARBONATE COMPOUND

[75] Inventors: Yoshihisa Kiso; Yuuichi, Matsunaga both of Yamaguchi, Japan

[73] Assignee: Mitsui Petrochemical Industries, Ltd., Tokyo, Japan

[21] Appl. No.: 338,200

[22] Filed: Apr. 14, 1989

[30] Foreign Application Priority Data

Apr. 16, 1988 [JP] Japan .................................. 63-92662
Apr. 16, 1988 [JP] Japan .................................. 63-92663

[51] Int. Cl.$^5$ ........................................... C07C 68/06
[52] U.S. Cl. ..................................... 558/270; 558/274
[58] Field of Search ............................... 558/270, 274

[56] References Cited

U.S. PATENT DOCUMENTS

| | | | |
|---|---|---|---|
| 4,552,704 | 11/1985 | Mark | 558/274 |
| 4,554,110 | 11/1985 | Mark | 558/274 |
| 4,609,501 | 9/1986 | Mark | 558/274 |

FOREIGN PATENT DOCUMENTS 2736062 2/1979 Fed. Rep. of Germany ...... 558/274

*Primary Examiner*—Jose G. Dees
*Attorney, Agent, or Firm*—Sherman and Shalloway

[57] ABSTRACT

Disclosed is a process for producing an aromatic carbonate which comprises reacting a phenolic compound with a di-aliphatic carbonate or an aliphatic-aromatic carbonate in the presence of a catalyst. The catalyst is either SnO and/or a tin compound represented by the following formula

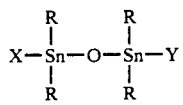

wherein X and Y are identical or different and each represents OH, SCN, OR$^1$, OCOR$^1$ or a halogen atom, R$^1$ represents an alkyl or aryl group, X and Y are not alkoxy groups at the same time, and R represents an alkyl or aryl group; or at least one compound of an element selected from the group consisting of Sc, Cr, Mo, W, Mn, Au, Ga, In, Bi, Te and lantanoids. The use of these specific catalysts enables the product to be obtained in high yields and selectivities and makes it easy to purify the product.

19 Claims, No Drawings

PROCESS FOR PRODUCTION OF AROMATIC CARBONATE COMPOUND

BACKGROUND OF THE INVENTION

(1) Field of the Invention

This invention relates to a process for producing an aromatic carbonate compound. More specifically, it relates to production of an easily purifiable aromatic carbonate compound in a high yield and a high selectivity by reacting a phenolic compound with a di-aliphatic carbonate or an aliphatic-aromatic carbonate in the presence of a specific catalyst.

(2) Description of the Prior Art

It is well known to produce an aliphatic-aromatic carbonate, a di-aromatic carbonate or an aromatic carbonate composed of a mixture of both by reacting a phenolic compound with a di-aliphatic carbonate or an aliphatic-aromatic carbonate. This reaction is shown by the following reaction equations.

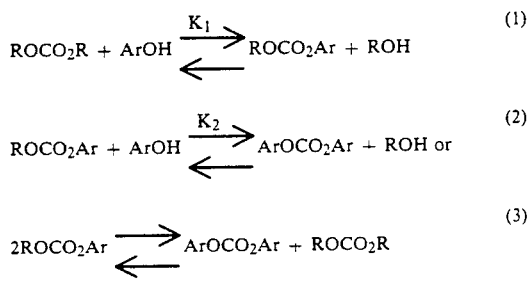

In the reactions (1) and (2), the equilibrium constants $K_1$ and $K_2$ shown below are low, the equilibrium is shifted to the starting material side, and the reaction rate is slow. Hence, the yields of $ROCO_2Ar$ and $ArOCO_2Ar$ are very low.

$$K_1 = \frac{[ROCO_2Ar][ROH]}{[ROCO_2R][ArOH]}$$

$$K_2 = \frac{[ArOCO_2Ar][ROH]}{[ROCO_2Ar][ArOH]}$$

Accordingly, many attempts have been made to select suitable catalysts for increasing the yield of the product in this reaction system.

For example, Japanese Laid-Open Patent Publication No. 105032/1976 discloses Lewis acids, metal compounds and transition metal compounds capable of forming Lewis acids, and cites $SnX_4$ (X is halogen, acetoxy, alkoxy or aryloxy) as preferred examples.

Japanese Laid-Open Patent Publication No. 48733/1979 discloses an organotin catalyst represented by the following formula $$(R^1)_{4-x}-SnO(Y)_x$$

wherein Y represents the $OCOR^2$ group, OH group or $OR^2$ group, $R^1$ and $R^2$ are identical or different and each represents an alkyl group having 1 to 12 carbon atoms, an aryl group having 6 to 12 carbon atoms. or an alkylaryl group having 7 to 12 carbon atoms, and x is an integer of 1 to 3,
which has no tin-halogen bond.

Japanese Laid-Open Patent Publication No. 63023/1979 discloses a tin alkoxide represented by the following formula $$R_{3-l}Sn(OR^1)_{1+l}$$

wherein R and $R^1$ represent a hydrocarbon group and l is an integer of 0 to 2.

Japanese Laid-Open Patent Publication No. 169444/1985 discloses a polymeric tin compound represented by the following formula

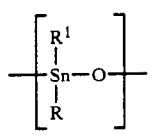

wherein R and $R^1$ represent a hydrocarbon group.

Japanese Laid-Open Patent Publication No. 169445/1985 discloses a tin compound of the following formula

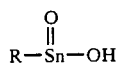

wherein R represents a hydrocarbon group or a hydrocarbon-oxy group.

Japanese Laid-Open Patent Publication No. 277345/1987 states that a tin compound represented by the following formula

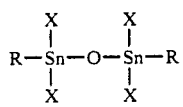

wherein R represents and alkyl group having 1 to 12 carbon atoms
can be used as a reaction catalyst for the production of aromatic carbonates.

These previously known tin-containing catalysts increase the yields of the products in the reaction systems to some extent, but still have insufficient catalytic activity. Accordingly, this makes it difficult to purify the products.

Japanese Laid-Open Patent Publication No. 105032/1976 cited above also describes $AlX_3$, $TiX_3$, $TiX_4$, $UX_4$, $VOX_3$, $VX_5$, $ZnX_2$, and $FeX_3$ (where X is halogen, acetoxy, alkoxy or aryloxy) as preferred examples of the Lewis acids and metal compounds and transition metal compounds capable of forming Lewis acids. However, the Lewis acids are corrosive and are not desirable for the reaction apparatus and the like. The method involving the use of the above compounds is low in the yield of the desired product, and cannot be said to be commercially advantageous.

SUMMARY OF THE INVENTION

The present invention is characterized by the fact that a phenolic compound is reacted with a di-aliphatic carbonate or an aliphatic aromatic carbonate in the presence of a specified catalyst.

It is an object of this invention to provide a process for producing aromatic carbonates in high yields within short periods of time by using catalysts having sufficient catalytic activity which are selected from compounds previously unknown as catalysts.

According to this invention, there is provided a process for producing an aromatic carbonate compound selected from aliphatic-aromatic carbonates, di-aromatic carbonates and mixtures of these, which comprises reacting a phenolic compound with a di-aliphatic carbonate or an aliphatic-aromatic carbonate in the presence of, as a catalyst, SnO and/or a tin compound represented by the following formula

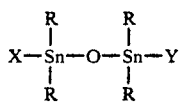

wherein X and Y are identical or different and each represents OH, SCN, OR$^1$, OCOR$^1$ or a halogen atom, R$^1$ represents an alkyl or aryl group, X and Y are not alkoxy groups at the same time, and R represents an alkyl or aryl group There is also provided a process for producing an aromatic carbonate compound selected from aliphatic-aromatic carbonates, di-aromatic carbonates and mixtures of these, which comprises reacting a phenolic compound with a di-aliphatic carbonate or an aliphatic-aromatic carbonate in the presence of, as a catalyst, at least one compound of an element selected from the group consisting of Sc, Cr, Mo, W, Mn, Au, Ga, In, Bi, Te and lanthanoids.

There is further provided a process for producing a diaromatic carbonate, which comprises further heating the aliphatic-aromatic carbonate obtained by the above processes or a mixture of it with a di-aromatic carbonate in the presence of a catalyst.

DETAILED DESCRIPTION OF THE PREFERRED EMBODIMENTS

The present invention is based on the new finding that in the reaction of a phenolic compound with a dialiphatic carbonate or an aliphatic-aromatic carbonate, the use of SnO and/or a tin compound of the following formula

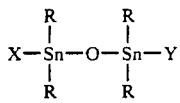

wherein X, Y and R are as defined above, can give an easily purifiable aromatic carbonate in a high yield and a high selectivity as compared with the use of known reaction catalysts.

In the process claimed in this aspect of the invention, various tin compounds may be used either singly or in combination with each other.

By using the specific tin compound as a catalyst, the reaction of a phenolic compound with a dialiphatic carbonate or an aliphatic-aromatic carbonate may be carried out at a wide range of temperatures ranging from 30° to 370° C., and particularly at 150° to 320° C., and the desired aromatic carbonate compounds can be produced in high yields and selectivities.

Japanese Laid-Open Patent Publication No. 63023/1979 discloses that in the production of aromatic carbonates, the reaction is carried out at a temperature of 20° to 300° C. This may seemingly suggest the reaction temperatures used in this invention. However, this patent document states that if the reaction temperature is too high, the catalyst will lose activity or the resulting carbonates undesirably undergo decomposition, and recommends the use of temperatures of not more than 250° C. as preferred reaction temperatures. In actual working examples given in the patent document, the reaction was carried out at a temperature of not more than 200° C.

In view of this fact, it is surprising that in the present invention, the reaction can be performed at a temperature of a wide range from 30° to 370° C. As stated hereinabove, when the aromatic carbonate compounds are to be obtained by the reactions (1) and (2), the equilibrium constants of the reaction, $K_1$ and $K_2$, are low and the rate of the reaction is low in the prior art. Hence, the yield of the desired product in the prior art is low. In order to remedy this defect of the prior art, the present inventors made extensive investigations, and found that while the equilibrium constants $K_1$ and $K_2$ are very low at a temperature of about 100° C., they surprisingly increase abruptly as the reaction temperature is elevated, and that when the reaction is carried out at temperatures of as high as 150° to 320° C., aromatic carbonates of high quality can be obtained in high yields and high selectivities within a short reaction time. In addition at such high temperatures, the aromatic carbonate compounds can be obtained in high yields by using the catalyst in small amounts. A further advantage is that since the amount of the catalyst is small and the desired product can be obtained within a short reaction time, side-reactions hardly occur, and the product is of excellent quality.

As shown in the above-cited Japanese Laid-Open Patent Publication No. 63023/1979, when the conventional catalyst are used at elevated temperatures, a by-product ether compound ArOR$^1$ (Ar and R$^1$ are as in formula (II) shown hereinafter) forms in addition to the desired aromatic carbonate compound. Furthermore, because the starting di-aliphatic carbonate or aliphatic-aromatic carbonate is decomposed, the selectivity of the aromatic carbonate undesirably decreases. The use of the catalyst specified in this invention offers the advantage that even at high reaction temperatures, the selectivity of the desired product is high, and that since the reaction solution is hardly colored and is a homogenous solution, the aromatic carbonate can be easily purified.

In the process of this invention, the mole ratio of the phenolic compound to the di-aliphatic carbonate or aliphatic-aromatic carbonate is from 5:1 to 1:5, but preferably about 1:1. The selectivity of the desired product is high, and the aromatic carbonate compound can be obtained at a high space time yield (STY) per unit volume of the reaction apparatus.

The conventional method in which to increase the yield of the aromatic carbonate, the reaction is carried out while the resulting ROH is removed out of the reaction system, and in which the equilibrium is thus shifted to the product side can also be applied to the process of this invention. In this case, too, since the equilibrium constants $K_1$ and $K_2$ in the reaction system are higher than in the prior art, ROH can be removed by, for example, distillation with a less tray number, and the yield can be increased more efficiently. If MeOCO$_2$Me is used as a material in the distillation operation MeOH azeotropes with MeOCO$_2$Me. When this azeotropic mixture is separated in a distillation column and only MeOH is removed, the yield of the aromatic carbonate is increased. Since in this case, the concentration of ROH becomes high owing to higher equilibrium constants $K_1$ and $K_2$, the removal of ROH by distillation becomes easy and expenses that go into equipment and utility can be curtailed to economic advantage. ROH can be more efficiently removed from the reaction mixture if as in the prior art, an azeotropic agent such as benzene or heptane is added to the reaction system and ROH is removed as an azeotrope with the azeotropic agent.

The reaction time is 2 minutes to 10 hours, preferably 10 minutes to 3 hours, and the process of this invention is economically better than the conventional methods which require a reaction time of 8 to 24 hours on an average.

In another aspect of the invention, the above reaction is carried out in the presence of, as a catalyst, at least one compound of an element selected from the group consisting of Sc, Cr, Mo, W, Mn, Au, Ga, In, Bi, Te and lanthanoids. This process is based on the new finding that by using the above catalyst, the aromatic carbonate compound can be produced in high yields, and the separation of the product and the recovery of the catalyst can be carried out easily.

The above catalyst compounds show excellent catalytic activity when used singly. If desired, two or more of them may be used in combination.

The reaction in this aspect of the process of this invention may be carried out at a temperature of 30° to 370° C., and particularly at 150° to 320° C., the desired product can be obtained in high yields within a short reaction time.

The reaction time may vary depending upon the type and amount of the catalyst and the reaction temperature, and is 2 minutes to 40 hours, preferably 10 minutes to 3 hours. If the reaction temperature is 230° C. or higher, the equilibrium constants of the reaction, $K_1$ and $K_2$, become high, and the reaction can be completed within a period of as short as 10 minutes to 1 hour. In this case, a product of excellent quality can be obtained in addition to the economical advantage of shortening the reaction time.

The mole ratio of the phenol compound to the dialiphatic carbonate or aliphatic-aromatic carbonate used in this reaction may be the same as described above with regard to the first aspect of the process of this invention. Preferably, the mole ratio is about 1:1, and in this case, the desired aromatic carbonate product has a high selectivity and can be obtained at a high space time yield per unit volume of the reaction apparatus.

The conventional method in which to increase the yield of the aromatic carbonate, the reaction is carried out while removing ROH out of the reaction system and thus the equilibrium is shifted to the product side may also be applied to this aspect of the process of this invention. Furthermore, as in the prior art, it is possible to add an azeotropic agent such as benzene or heptane to the reaction system and remove ROH as an azeotrope with the azeotropic agent. This enables more efficient removal of ROH.

The starting compounds and the catalyst used in this invention and the products obtained will be described below in detail.

Phenolic Compound

The phenolic compounds used in this invention are represented by the following formula ArOH [I]

wherein Ar represents an aromatic compound residue, for example, a substituted or unsubstituted benzene, naphthalene, antharacene or tetralin ring.

Specific examples of the phenolic compounds of formula [I] include phenol, o-, m- or p-cresol, o-, m-or p-chlorophenol, o-, m- or p-ethylphenol, o-, m- or p-(iso)propylphenol, o-, m- or p-phenoxyphenol, o-, m- or p-phenylphenol, o-, m- or p-methoxyphenol, o-, m- or p-nitrophenol, 2,6-dimethylphenol, 2,4-dimethylphenol, 3,4-dimethylphenol, 2,6-dibutylphenol, alpha-naphthol, beta-naphthol and beta-anthrol. Of these, phenol is most preferably used.

Di-aliphatic carbonates

The di-aliphatic carbonates that can be used in this invention are represented by the following general formula

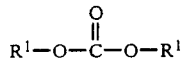
[II]

wherein $R^1$ represents a monovalent aliphatic hydrocarbon group, preferably an alkyl or cycloalkyl group. The two $R^1$ groups may be linked to each other. The alkyl group may be linear or branched alkyl group having 1 to 12 carbon atoms, and examples include methyl, ethyl, propyl, isopropyl, butyl. t-butyl, pentyl, neopentyl, hexyl, heptyl and octyl groups. Examples of the cycloalkyl group are cycloalkyl groups having 5 to 7 carbon atoms in the ring, and include cyclopentyl, methylcyclohexyl, cyclohexyl and cycloheptyl groups. An ethylene group may be cited as an example of two $R^1$ groups linked to each other.

Specific examples of the compounds represented by general formula [II] include dimethyl carbonate, diethyl carbonate, di-n-butyl carbonate, dicyclohexyl carbonate, dibenzyl carbonate, di-n-octyl carbonate, diisopropyl carbonate and ethylene carbonate. Of these, dimethyl carbonate is preferably used.

Aliphatic-Aromatic Carbonates

The aliphatic-aromatic carbonates that may be used in this invention are represented by the following general formula (III)

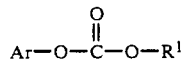
(III)

wherein Ar is as defined in formula (I), and $R^1$ is as defined in formula (II). Specific examples include phenylmethyl carbonate, phenylethyl carbonate, phenylcyclohexyl carbonate and tolylmethyl carbonate. Of these, phenylmethyl carbonate is preferably used when the reaction is to be carried out in the presence of the specific catalyst.

Aromatic carbonate compounds

The aromatic carbonate compound as the product in this invention is an aliphatic-aromatic carbonate, a diaromatic carbonate or a mixture of both. The diaromatic carbonate is represented by the formula

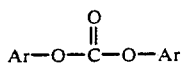

wherein Ar is as defined in formula (I). Specific examples are diphenyl carbonate di(methylphenyl) carbonate, di(dimethylphenyl) carbonate and dinaphthyl carbonate.

Catalysts (1) Tin compound catalysts are SnO and/or metal compounds of the following formula

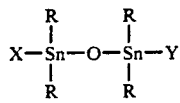

wherein X, Y and R are as defined above. Specific examples of the metal compounds include
a (R=Bu, X=Cl, Y=Cl), b (R=Bu, X=Cl, Y=OH), c (R=Bu, X=Cl, Y=OPh), d (R=Bu, X=Br, Y=Br), c (R =Bu, X=Br, Y=OH), f (R=Bu, X=Br, Y=OPh), g (R=Bu, X=NCS, Y=NCS), h (R=Bu, X=NCS, Y=OH), i (R=Bu, X=NCS, Y=OPh), j (R=Bu, X=NCS, Y=OCH$_3$), k (R=Bu, X=Cl, Y=CH$_2$Ph), l (R=Bu, X=OAc, Y=OAc), m (R=Et, X=Cl, Y=Cl), n (R =Et, X=NCS, Y=NCS), o (R=Me, X =Cl, Y=Cl), p (R=Me, X=OAc, Y=OAc) and q (R=Ph, X=Cl, Y=Cl)

These catalysts show excellent catalyst activity even when used singly. If desired, however, they may be used in combination with each other.

(2) Catalyst comprising Sc, Cr, Mo, W, Mn, Au, Ga, In, Bi, Te and lanthanoids

This catalyst is at least one compound of an element selected from the group consisting of Sc, Cr, Mo, W, Mn, Au, Ga, In, Bi, Te and lanthanoids. Compounds of Sc, Mo, Mn, Au, Bi and lanthanoids have high catalytic activity and the desired products can be obtained in high yields.

Specific examples of such catalysts include
Sc$_2$O$_3$, ScC$_2$, Sc(OH)$_3$, ScCl$_3$, ScF$_3$;
Mo(CH$_3$COCHCOCH$_3$)$_3$, Mo(CO)$_6$, Mo$_2$O$_3$, Mo(OH)$_3$, MoO$_2$, C$_5$H$_5$MoC$_6$H$_6$;
Mn$_2$(CO)$_{10}$, Mn(CH$_3$COCHCOCH$_3$)$_3$, MnO$_2$, KMnO$_4$, Mn$_2$O$_7$, MnCl$_2$;
NaAuCl$_2$2H$_2$O, Aucl$_3$, Auf$_3$;
Bi(OCOCH$_3$), BiH$_3$, Mg$_3$Bi$_2$;
La(OCOCH$_3$)$_2$, La(OH)$_3$, Ce(OH)$_3$, Pr(OH)$_3$, Nd(OH)$_3$, Pm(OH)$_3$, Sm(OH) , Eu(OH)$_3$, Gd(OH)$_3$, Lu(OH)$_3$, LuCl$_3$, 6H$_2$O, La(NO$_3$)$_3$ La$_2$O$_3$;
Cr(CH$_3$COCHCOCH$_3$)$_3$, Cr(CO)$_6$, Cr$_2$O$_3$, Cr(OH)$_3$, K$_2$Cr$_2$O$_7$, (NH$_4$)$_2$Cr$_2$O$_7$, Cr(H$_2$O)$_6$Cl$_3$, CrO$_3$;
W(CO)$_6$, WO$_2$, WO$_3$, WF$_6$, WCl$_6$, WBr$_6$;
Ga(NO$_3$)$_3$, GaCl$_2$, GaCl$_3$;
In$_2$O$_3$, (InH$_3$)$_n$, InCl$_2$;
TeCl$_4$, THE$_2$, TeF$_6$, TeO$_2$, TeCl$_4$, H$_2$TeCl$_6$ and TeO.

Preferred among them are Sc$_2$O$_3$, Mo(CH$_3$COCHCOCH$_3$)$_3$,
Mo(CO)$_6$, Mn$_2$(CO)$_{10}$, Mn(CH$_3$COCHCOCH$_3$)$_3$, NaAuCl$_2$.2H$_2$O, Bi(OCOCH$_3$), La(OCOCH$_3$)$_2$ and LuCl$_3$.6H$_2$O.

These catalysts show excellent catalytic activity even when used singly. If desired, however, they may be used in combination with each other.

The amount of the catalyst (1) or (2) is an amount generally called a catalytic amount, which is effective for catalyzing the ester interchange reaction of the phenolic compound with the aliphatic-aromatic carbonate. It is generally used in an amount of 10 to $10^{-4}$ mole %, preferably 0.2 to $10^{-3}$ mole %, based on the amount of the phenolic compound.

Di-aromatic carbonates may be produced by heating the aliphatic-aromatic carbonate or a mixture of it with a di-aromatic carbonate obtained by the process set forth in claim 1 or 2 further in the presence of a catalyst.

The catalyst may be the same as the one used in the previous step, but may be a different catalyst selected from those described hereinabove.

This reaction is shown by the above reaction equation (3), and may be carried out at a reaction temperature of 50° to 370° C., preferably 150° to 320° C., under elevated, atmospheric or reduced pressure. Preferably, it is carried out under reduced pressure while removing the resulting di-aliphatic carbonate out of the reaction system.

Thus, by reacting the phenolic compound with the di-aliphatic carbonate or the aliphatic-aromatic carbonate in the presence of a highly active catalyst composed of SnO and/or a tin compound represented by the following formula

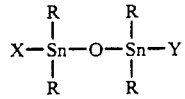

wherein X, Y and R are as defined above,
an aromatic carbonate can be obtained in high yields and selectivities. Since the reaction solution is not colored, it can be easily purified to obtain a pure aromatic carbonate.

Furthermore, according to this invention, an aromatic carbonate can be produced in high yields by carrying out the above reaction in the presence of a catalyst composed of at least one compound of an element selected from the group consisting of Sc, Cr, Mo, W, Mn, Au, Ga, In, Bi, Te and lanthanoids. According to this process, isolation of the product and the recovery of the catalyst can be easily performed. This advantage is greater when at least one compound of an element selected from Sc, Mo, Mn, Au, Bi and lanthanoids is used as the catalyst.

The following examples illustrate the present invention in greater detail. Examples 1 to 13 and Comparative Example 1 illustrate the use of tin-containing catalysts, and Examples 14 to 26, the use of the other type of catalysts.

EXAMPLE 1

Phenol (0.11 mole), 0.11 mole of dimethyl carbonate (DMC) and 0.01 g of Cl$^n$Bu$_2$SnOSn$^n$Bu$_2$(OH) were put in a 50 ml. autoclave, and heated at 265° C. for 30 minutes. After the reaction, the reaction solution was a yellowish nearly colorless, uniform solution. Its gas chromatographic analysis showed that the conversion of phenol was 12.46%, the yield of phenylmethyl carbonate (PMC) based on phenol was 12.04%, the yield of anisole was 0.42%, and the selectivity of PMC was 96.6%.

EXAMPLES 2-8

Example 1 was repeated except that the reaction temperature and the amounts of the starting materials and the catalyst were changed. The results are shown in Table 1.

EXAMPLES 9-12

Example 1 was repeated except that the reaction temperature and the catalyst were changed as indicated in Table 1. The results are shown in Table 1. The reaction solutions were colorless or slightly yellowish uniform solutions.

COMPARATIVE EXAMPLE 1

Example 1 was repeated except that $SnCl_4$ was used as the catalyst and the reaction temperature was changed to 280° C. The results are shown in Table 1. The reaction solution was brown, and a black precipitate formed.

EXAMPLE 14

Phenol (0.11 mole), 0.11 mole of dimethyl carbonate and 0.01 g of $Mn_2(CO)_{10}$ were put in a 50 ml. autoclave, and heated at 250° C. for 30 minutes. Gas chromatographic analysis of the reaction solution showed that the conversion of phenol was 15.17%, and anisole, phenylmethyl carbonate (PMC) and diphenyl carbonate (DPC) formed in a yield of 1.78%, 12.50%, and 0.89%, respectively, based on phenol. The total selectivity of PMC and DPC and 88.3%.

EXAMPLES 15-25

Example 14 was repeated except that the catalysts indicated in Table 2 were used instead of the catalyst used in Example 14. The results are shown in Table 2.

EXAMPLE 26

Phenylmethyl carbonate (7 millimole) and 0.01 g of $Mn_2(CO)_{10}$ were heated in an autoclave at 200° C. for 1 hour. Gas chromatographic analysis of the reaction solution showed that 1.7 millimoles of diphenyl carbonate and 1.7 millimoles of dimethyl carbonate formed.

TABLE 1

| Example No. | Starting Materials phenol | Starting Materials DMC | Catalyst Compounds[2] | Catalyst g | Reaction Conditions (°C./hr) | Yield of the products (based on phenol, %) anisole | PMC | DPC[1] | Convention of phenol (%) | Selectivity of PMC + DPC (%) |
|---|---|---|---|---|---|---|---|---|---|---|
| 1 | 0.11 | 0.11 | Cl$^n$Bu$_2$SnOSn$^n$Bu$_2$(OH) | 0.01 | 265/0.5 | 0.42 | 12.04 | 0 | 12.46 | 96.6 |
| 2 | 0.11 | 0.11 | Cl$^n$Bu$_2$SnOSn$^n$Bu$_2$(OH) | 0.01 | 200/0.5 | 0 | 5.32 | 0 | 5.32 | 100 |
| 3 | 0.11 | 0.11 | Cl$^n$Bu$_2$SnOSn$^n$Bu$_2$(OH) | 0.01 | 225/0.5 | 0.19 | 6.92 | 0 | 7.10 | 97.3 |
| 4 | 0.11 | 0.11 | Cl$^n$Bu$_2$SnOSn$^n$Bu$_2$(OH) | 0.01 | 250/0.5 | 0.11 | 11.70 | 0 | 11.81 | 99.1 |
| 5 | 0.11 | 0.11 | Cl$^n$Bu$_2$SnOSn$^n$Bu$_2$(OH) | 0.01 | 280/0.5 | 1.11 | 14.94 | 0 | 16.05 | 93.1 |
| 6 | 0.11 | 0.11 | Cl$^n$Bu$_2$SnOSn$^n$Bu$_2$(OH) | 0.01 | 298/0.5 | 1.13 | 15.16 | 1.20 | 20.33 | 80.5 |
| 7 | 0.11 | 0.11 | Cl$^n$Bu$_2$SnOSn$^n$Bu$_2$(OH) | 0.01 | 353/0.5 | 7.80 | 14.12 | 3.61 | 32.90 | 53.9 |
| 8 | 0.11 | 0.05 | Cl$^n$Bu$_2$SnOSn$^n$Bu$_2$(OH) | 0.01 | 283/0.5 | 1.34 | 7.75 | 0 | 9.09 | 85.3 |
| 9 | 0.11 | 0.11 | SnO | 0.01 | 250/0.5 | 0.16 | 12.52 | 0.70 | 13.38 | 98.8 |
| 10 | 0.11 | 0.11 | Cl$^n$Bu$_2$SnOSn$^n$Bu$_2$Cl | 0.01 | 250/0.5 | 0.10 | 12.76 | 0.52 | 13.38 | 99.3 |
| 11 | 0.11 | 0.11 | (NCS)$^n$Bu$_2$SnOSn$^n$—Bu$_2$(OCH$_3$) | 0.01 | 250/0.5 | 0.10 | 12.70 | 0.30 | 13.10 | 99.2 |
| 12 | 0.11 | 0.11 | (CH$_3$CO$_2$)$^n$Bu$_2$SnO—Sn$^n$Bu$_2$(OCCH$_3$) | 0.01 | 250/0.5 | 0.11 | 11.60 | 0 | 11.71 | 99.1 |
| Comparative Example 1 | 0.11 | 0.11 | SnCl$_4$ | 0.01 | 280/0.5 | 4.88 | 10.82 | 0 | 15.70 | 68.9 |

[1]DPC = diphenyl carbonate.
[2]$^n$Bu: normal butyl

TABLE 2

| Example No. | Catalyst | Yields of the products (based on phenol, %) anisole | PMC | DMC | Conversion of phenol (%) | Selectivity of PMC + DPC (%) |
|---|---|---|---|---|---|---|
| 14 | Mn(CO)$_{10}$ | 1.78 | 12.50 | 0.89 | 15.17 | 88.3 |
| 15 | Sc$_2$O$_3$ | 0.37 | 7.24 | 0 | 7.63 | 95.1 |
| 16 | Mo(CH$_3$COCHCOCH$_3$)$_3$ | 0.21 | 7.68 | 0 | 7.89 | 97.3 |
| 17 | NaAuCl$_2$.2H$_2$O | 4.12 | 7.93 | 0 | 12.03 | 65.8 |
| 18 | Bi(OCOCH$_3$) | 0.45 | 7.67 | 0.40 | 8.52 | 94.7 |
| 19 | La(OCOCH$_3$)$_2$.1.5H$_2$O | 2.92 | 8.34 | 0 | 11.26 | 74.1 |
| 20 | LuCl$_3$.6H$_2$O | 1.91 | 11.02 | 0.67 | 13.60 | 86.0 |
| 21 | Cr(CH$_3$COCHCOCH$_3$)$_3$ | 0.36 | 3.00 | 0 | 3.36 | 89.3 |
| 22 | W(CO)$_6$ | 0.31 | 3.39 | 0 | 3.70 | 91.6 |
| 23 | Ga(NO$_3$)$_3$.H$_2$O | 0.21 | 4.54 | 0 | 4.75 | 95.6 |
| 24 | In$_2$O$_3$ | 0.42 | 3.72 | 0 | 4.14 | 89.9 |
| 25 | TeCl$_4$ | 0.17 | 3.04 | 0 | 3.21 | 94.7 |

EXAMPLE 13

Phenylmethyl carbonate (7 millimoles) and 0.01 g of Cl$^n$Bu$_2$SnO$^n$Bu$_2$ (OH) were heated in an autoclave at 200° C. for 1 hour. Analysis of the reaction solution by gas chromatography showed that 1.8 millimoles of diphenyl carbonate and 1.8 millimoles of dimethyl carbonate formed.

We claim:

1. A process for producing an aromatic carbonate compound selected from aliphatic-aromatic carbonates, di-aromatic carbonates and mixtures of these, which comprises reacting a phenolic compound with a di-aliphatic carbonate or an aliphatic-aromatic carbonate in the presence of, as a catalyst, SnO and/or a tin compound represented by the following formula

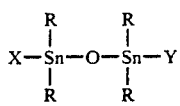

wherein X and Y are identical or different and each represents OH, SCN, OR$^1$, OCOR$^1$ or a halogen atom, R$^1$ represents an alkyl or aryl group, X and Y are not OR$^1$ groups at the same time, and R represents an alkyl or aryl group.

2. The process of claim 1 wherein the catalyst is SnO.

3. The process of claim 1 wherein the catalyst is a tin compound of said formula.

4. The process of claim 3 wherein R is butyl.

5. The process of claim 4 wherein x represents bromine or chlorine and Y represents bromine, chlorine or hydroxyl.

6. A process for producing an aromatic carbonate compound selected from aliphatic-aromatic carbonates, di-aromatic carbonates and mixtures of these which comprises reacting a phenolic compound with a di-aliphatic carbonate or an aliphatic-aromatic carbonate in the presence of, as a catalyst, at least one compound of an element selected from the group consisting of Sc, Cr, Mo, W, Mn, Au, Ga, In, Bi, Te and lanthanoids.

7. The process of claim 1 or 6 in which the reaction is carried out at a temperature of 150° to 320° C.

8. The process of claim 1 or 6 in which the mole ratio of the phenolic compound to the di-aliphatic carbonate or aliphatic-aromatic carbonate is from 5:1 to 1:5.

9. The process of claim 1 or 6 in which the catalyst is used in a concentration of 0.2 mole % to 10$^{-3}$ mole % based on the phenolic compound.

10. The process of claim 1 or 6 in which the phenolic compound is phenol.

11. The process of claim 1 or 6 in which the dialiphatic carbonate is dimethyl carbonate.

12. The process of claim 1 or 6 in which the aliphatic-aromatic carbonate is methylphenyl carbonate.

13. The process of claim 6 in which the catalyst is at least one compound of at least one element selected from the group consisting of Sc, Mo, Mn, Au, Bi and lanthanoids.

14. The process of claim 6 wherein said catalyst is a compound selected from the group consisting of:
Sc$_2$O$_3$, ScC$_2$, Sc(OH)$_3$, ScCl$_3$, ScF$_3$;
Mo(CH$_3$COCHCOCH$_3$)$_3$, Mo(CO)$_6$, Mo$_2$O$_3$, Mo(OH)$_3$, MoO$_2$, C$_5$H$_5$MoC$_6$H$_6$;
Mn$_2$(CO)$_{10}$, Mn(CH$_3$COCHCOCH$_3$)$_3$, MnO$_2$, MnO$_4$, Mn$_2$O$_7$, MnCl$_2$;
NaAuCl$_2$2H$_2$O, AuCl$_3$, AuF$_3$;
Bi(OCOCH$_3$), BiH$_3$, Mg$_3$Bi$_2$;
La(OCOCH$_3$)$_2$, La(OH)$_3$, Ce(OH)$_3$, Pr(OH)$_3$, Nd(OH)$_3$, Pm(OH)$_3$, Sm(OH) , Eu(OH)$_3$, Gd(OH)$_3$, Lu(OH)$_3$, LuCl$_3$, 6H$_2$O, La(NO$_3$)$_3$ La$_2$O$_3$;
Cr(CH$_3$COCHCOCH$_3$)$_3$, Cr(CO)$_6$, Cr$_2$O$_3$, Cr(OH)$_3$, K$_2$Cr$_2$O$_7$, (NH$_4$)$_2$Cr$_2$O$_7$, Cr(H$_2$O)$_6$Cl$_3$, CrO$_3$;
W(CO)$_6$, WO$_2$, WO$_3$, WF$_6$, WCl$_6$, WBr$_6$;
Ga(NO$_3$)$_3$, GaCl$_2$, GaCl$_3$;
In$_2$O$_3$, (InH$_3$)$_n$, InCl$_2$;
TeCl$_4$, TeH$_2$, TeF$_6$, TeO$_2$, TeCl$_4$, H$_2$TeCl$_6$ and TeO.

15. The process of claim 6 wherein the catalyst is a compound selected from the group consisting of Sc$_2$O$_3$, Mo(CH$_3$COCHCOCH$_3$)$_3$, Mo(CO)$_6$, Mn$_2$(CO)$_{10}$, Mn(CH$_3$COCHCOCH$_3$)$_3$, NaAuCl$_2$.H$_2$O, Bi(OCOCH$_3$), La(OCOCH$_3$)$_2$ and LuCl$_3$.6H$_2$O.

16. The process of claim 7 in which the reaction is carried out for from 10 minutes to 3 hours.

17. The process of claim 1 or 2 in which the reaction is carried out at a temperature of 230° C. or higher for a period of from about 10 minutes to 1 hour.

18. A process for producing a di-aromatic carbonate, which comprises preparing an aliphatic-aromatic carbonate or a mixture thereof with a di-aromatic carbonate by reacting a phenolic compound with a di-aliphatic carbonate or an aliphatic-aromatic carbonate in the presence of, as a catalyst, a member selected from the group consisting of (A) SnO, (B) a tin compound represented by the formula:

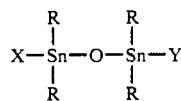

wherein X and Y are identical or different and each represents OH, SCN, OR$^1$, OCOR$^1$ or a halogen atom, R$^1$ represents an alkyl or aryl group, X and Y are not OR$^1$ groups at the same time, and R represents an alkyl or aryl group, (C) mixtures of (A) and (B), and (D) at least one compound of an element selected from the group consisting of Sc, Cr, Mo, W, Mn, Au, Ga, In, Bi, Te and lanthanoids and heating the resulting aliphatic-aromatic carbonate or its mixture with di-aromatic carbonate in the presence of said catalyst (A), (B) or (C).

19. A process for producing a di-aromatic carbonate, which comprises preparing an aliphatic-aromatic carbonate or a mixture thereof with a di-aromatic carbonate by reacting a phenolic compound with a di-aliphatic carbonate or an aliphatic-aromatic carbonate in the presence of, as a catalyst, a member selected from the group consisting of (A) SnO, (B) a tin compound represented by the formula:

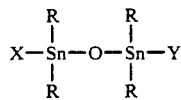

wherein X and Y are identical or different and each represents OH, SCN, OR$^1$, OCOR$^1$ or a halogen atom, R$^1$ represents an alkyl or aryl group, X and Y are not OR$^1$ groups at the same time, and R represents an alkyl or aryl group, (C) mixtures of (A) and (B), and (D) at least one compound of an element selected from the groups consisting of Sc, Cr, Mo, W, Mn, Au, Ga, In, Bi, Te and lanthanoids and heating the resulting aliphatic-aromatic carbonate or its mixture with di-aromatic carbonate in the presence of said catalyst (D).

* * * * *